United States Patent
Peters

(10) Patent No.: US 10,583,238 B2
(45) Date of Patent: Mar. 10, 2020

(54) PORTABLE ULTRAFILTRATION UNIT AND DEVICE FOR SUPPLYING THE ULTRAFILTRATION UNIT WITH DIALYSIS FLUID

(71) Applicant: FRESENIUS MEDICAL CARE DEUTSCHLAND GMBH, Bad Homburg (DE)

(72) Inventor: Arne Peters, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 36 days.

(21) Appl. No.: 15/746,014

(22) PCT Filed: Jul. 26, 2016

(86) PCT No.: PCT/EP2016/067834
§ 371 (c)(1),
(2) Date: Jan. 19, 2018

(87) PCT Pub. No.: WO2017/021236
PCT Pub. Date: Feb. 9, 2017

(65) Prior Publication Data
US 2018/0207345 A1 Jul. 26, 2018

(30) Foreign Application Priority Data
Aug. 6, 2015 (DE) .......................... 10 2015 010 316

(51) Int. Cl.
*A61M 1/34* (2006.01)
*A61M 1/16* (2006.01)

(52) U.S. Cl.
CPC ............ *A61M 1/3482* (2014.02); *A61M 1/16* (2013.01); *A61M 1/1635* (2014.02);
(Continued)

(58) Field of Classification Search
None
See application file for complete search history.

(56) References Cited

U.S. PATENT DOCUMENTS 4,269,708 A 5/1981 Bonomini et al.
8,040,493 B2 * 10/2011 Fulkerson ........... A61M 1/3663
356/28
(Continued)

FOREIGN PATENT DOCUMENTS

| JP | S55158056 A | 12/1980 |
| WO | 2009051669 A1 | 4/2009 |
| WO | 2009083011 A2 | 7/2009 |

OTHER PUBLICATIONS

International Search Report and Written Opinion issued in corresponding International Patent Application No. PCT/EP2016/067834 (with English translation of International Search Report) dated Oct. 4, 2016 (14 pages).
(Continued)

*Primary Examiner* — Ana M Fortuna
(74) *Attorney, Agent, or Firm* — Kilyk & Bowersox, P.L.L.C.

(57) ABSTRACT

The invention relates to a portable ultrafiltration unit A which comprises a blood pump 7 for conveying blood and an ultrafiltration pump 6 for conveying ultrafiltrate. The invention further relates to a stationary device B for supplying dialysate to the portable ultrafiltration unit A, and to a medical treatment system which comprises an ultrafiltration unit and a device for supplying dialysate to the ultrafiltration unit. The ultrafiltration unit according to the invention is in the form of a unit to be connected to a stationary device for supplying dialysate to the ultrafiltration unit, in such a way that a fluid connection can be established for feeding in fresh dialysate and removing used dialysate. As a result, the ultrafiltration unit can not only be used for ultrafiltration, but also, when used in conjunction with the stationary device for supplying dialysate to the ultrafiltration unit, for a blood treatment as carried out by a conventional blood treatment device. It is merely necessary to connect the
(Continued)

Figure 2A:
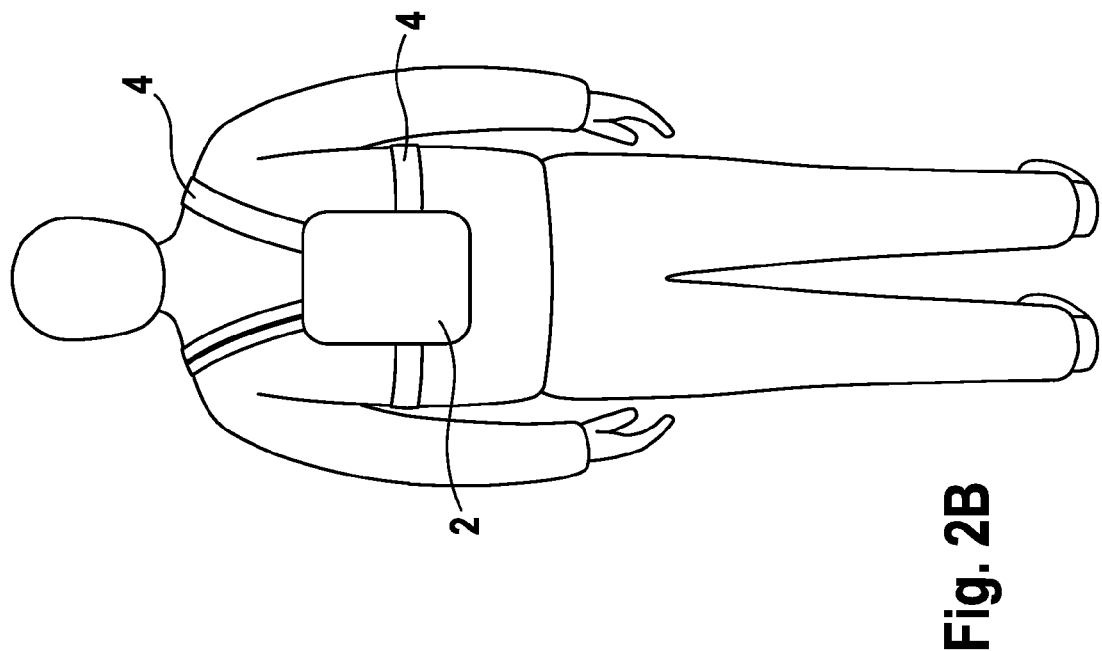

ultrafiltration unit A to the device B for supplying dialysate to the ultrafiltration unit. There is no need to detach the patient connections 27A, 27B of the venous and arterial blood lines 27, 28 or to attach said connections to the patient, as result of which the preparation time for a blood treatment can be reduced.

19 Claims, 3 Drawing Sheets

(52) U.S. Cl.
CPC ............ *A61M 1/1672* (2014.02); *A61M 1/34* (2013.01); *A61M 1/3413* (2013.01); *A61M 1/3417* (2014.02); *A61M 2205/50* (2013.01); *A61M 2205/505* (2013.01); *A61M 2209/088* (2013.01)

(56) References Cited

U.S. PATENT DOCUMENTS

| | | |
|---|---|---|
| 2004/0254514 A1 | 12/2004 | Gura |
| 2007/0179425 A1 | 8/2007 | Gura et al. |
| 2009/0008306 A1* | 1/2009 | Cicchello et al. |
| 2009/0120864 A1 | 5/2009 | Fulkerson et al. |
| 2010/0192686 A1* | 8/2010 | Kamen ................ A61M 1/16 73/290 R |
| 2011/0315611 A1* | 12/2011 | Fulkerson ........... A61M 1/3639 210/96.2 |
| 2012/0289881 A1 | 11/2012 | Lyu et al. |
| 2013/0213890 A1 | 8/2013 | Kelly et al. |
| 2013/0274642 A1* | 10/2013 | Soykan et al. |
| 2013/0292312 A1 | 11/2013 | Heide et al. |

OTHER PUBLICATIONS

International Preliminary Report on Patentability issued in corresponding International Patent Application No. PCT/EP2016/067834 dated Feb. 6, 2018 (7 pages).

Office Action received in corresponding Japanese Patent Application No. 2018-505727 dated Feb. 26, 2019 (English translation attached) (9 pages).

* cited by examiner

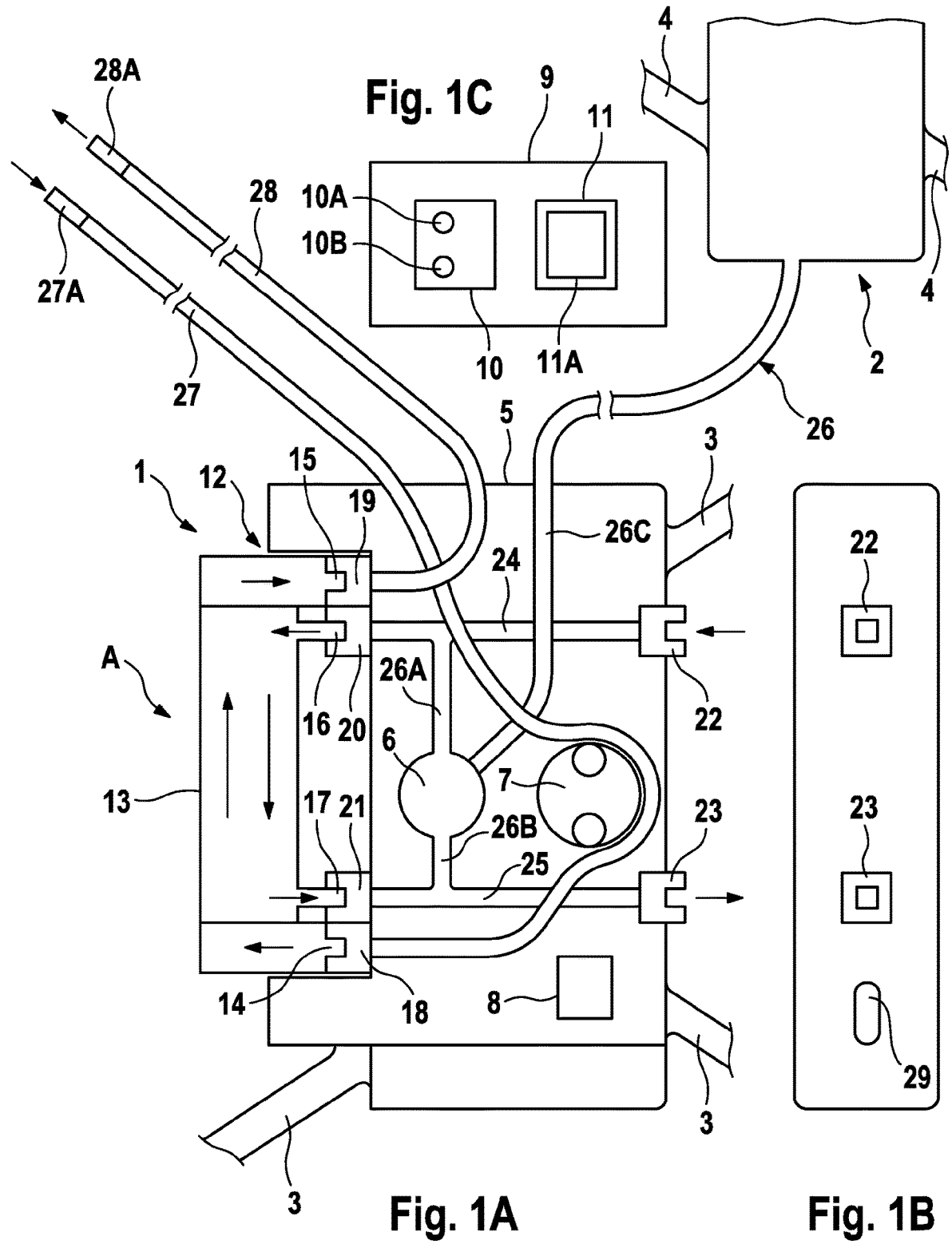

PORTABLE ULTRAFILTRATION UNIT AND DEVICE FOR SUPPLYING THE ULTRAFILTRATION UNIT WITH DIALYSIS FLUID

This application is a National Stage Application of PCT/EP2016/067834, filed Jul. 26, 2016, which claims priority to German Patent Application No. 10 2015 010 316.4, filed Aug. 6, 2015.

The invention relates to a portable ultrafiltration unit which comprises a blood pump for conveying blood and an ultrafiltration pump for conveying ultrafiltrate. The invention further relates to a stationary device for supplying the ultrafiltration unit with dialysate and to a medical treatment system which comprises a portable ultrafiltration unit and a stationary device for supplying dialysate to the ultrafiltration unit.

In the event of chronic kidney failure, various methods for apparatus-based blood treatment are used to remove substances which are normally eliminated with urine and to remove fluid. In haemodialysis (HD), substance transport over the semipermeable membrane of a filter is predominantly diffusive, whereas in haemofiltration (HF) substance transport over the filter membrane is convective. A combination of the two methods is called haemodiafiltration (HDF).

The known devices for carrying out the aforementioned blood treatment methods comprise an extracorporeal blood circuit and a dialysate system. The extracorporeal blood circuit comprises an arterial blood line which leads to a blood chamber of a filter (dialyser) divided into a first chamber and a second chamber by a semipermeable membrane, and a venous blood line which leads away from the first chamber. The dialysate system comprises a dialysate feed line leading to the second chamber of the filter and a dialysate removal line leading away from the second chamber of the filter.

Owing to the high volumes exchanged, the volume of the fluid fed to the patient and the volume of fluid removed has to be precisely balanced over the entire duration of the treatment. Therefore, the known devices for extracorporeal blood treatment have a balancing unit.

The extracorporeal blood treatments are carried out at intervals of from two to three days, for example. In addition to the blood being cleaned, the aim of an optimum renal replacement therapy is also to adjust the serum volume in the blood. During the blood treatment, a specific volume of ultrafiltrate is thus removed from the extracorporeal blood circuit by means of the filter membrane. For example, approximately three litres of fluid are removed from the patient. Once the fluid has been removed, the serum volume in the blood increases again between treatments. In patients with a significantly elevated serum volume in the blood, it may not be possible for the blood treatment to be completed within the intended time owing to the desired ultrafiltration target not being reached.

For an optimum renal replacement therapy, it would be advantageous to have blood treatments at intervals that are as short as possible. However, shortening the time between the treatments is not only a great burden on the patient, but also creates a logistical problem.

In addition to the stationary blood treatment devices which allow various blood treatments to be carried out, for example haemodialysis (HD), haemofiltration (HF) or haemodiafiltration (HDF), portable devices are also known, which, however, can only be used to carry out haemofiltration (HF). The portable ultrafiltration devices only comprise the components of a stationary blood treatment device that are required for ultrafiltration. As a result, the ultrafiltration can be carried out in a relatively simple manner.

The problem addressed by the invention is to further simplify the apparatus required for carrying out blood treatments and to reduce the time needed therefor.

This problem is solved according to the invention by the features of claims 1 and 12. The dependent claims relate to advantageous embodiments of the invention.

In the form of an independent unit, the ultrafiltration unit according to the invention allows a haemofiltration treatment (ultrafiltration) to be carried out in a relatively simple manner in terms of apparatus since the ultrafiltration unit only has the components required for the ultrafiltration. The patient can be treated using the ultrafiltration unit not only in the clinic, but also at home. By means of the ultrafiltration unit, additional ultrafiltrations can be carried out at shorter intervals between the blood treatments using a stationary dialysis machine. The patient can carry the ultrafiltration unit with them as a portable unit. The simple technical design of the ultrafiltration unit allows for battery-powered operation.

However, the ultrafiltration unit according to the invention not only allows fluid to be removed in the time between the blood treatments, but rather said unit is also formed as a unit to be connected to a stationary device for supplying dialysate to the ultrafiltration unit, in such a way that a fluid connection can be established for feeding in fresh dialysate and removing used dialysate. As a result, the ultrafiltration unit can not only be used for a haemofiltration treatment (ultrafiltration), but also, when used in conjunction with the stationary device for supplying dialysate to the ultrafiltration unit, for blood treatments as carried out by a conventional blood treatment device, for example haemodialysis (HD).

Further advantages are produced upon use in conjunction with the stationary device for supplying dialysate to the ultrafiltration unit. In order to carry out a blood treatment, it is merely necessary to connect the ultrafiltration unit to the device for supplying dialysate to the ultrafiltration unit. There is no need to detach the patient connections of the venous and arterial blood lines or to attach said connections to the patient. Since the patient remains connected to the ultrafiltration unit, the preparation time for a blood treatment can be significantly reduced by means of the portable ultrafiltration unit.

The device according to the invention for supplying dialysate to the ultrafiltration unit has an apparatus for providing fresh dialysate, an apparatus for removing used dialysate, and a balancing unit for balancing fresh and used dialysate, the device for supplying dialysate to the ultrafiltration unit being designed such that a fluid connection can be established for feeding fresh dialysate to the ultrafiltration unit and removing used dialysate from the ultrafiltration unit.

One or more portable ultrafiltration units and one or more devices for supplying dialysate to the ultrafiltration unit form the medical treatment system according to the invention.

The ultrafiltration unit according to the invention can be connected to a device which only contains the modules required for providing fresh dialysate and removing used dialysate, and for balancing fresh dialysate and used dialysate. The device for supplying dialysate to the ultrafiltration unit can, however, also be in the form of a device for extracorporeal blood treatment which comprises an extracorporeal blood circuit and a dialysate system. In this case, however, the ultrafiltration unit only uses the components for providing, removing and balancing the dialysate. The whole extracorporeal blood circuit or at least parts of the extracorporeal blood circuit can remain unused. This embodiment of the device for supplying dialysate to the ultrafiltration unit is advantageous in that the device can also be operated without the ultrafiltration unit.

Which components are used to establish a fluid connection is not important for the basic principle of the invention. The ultrafiltration unit preferably comprises a first dialysate connection for a feed line for fresh dialysate and a second dialysate connection for a removal line for used dialysate. The dialysate connections can have various designs. The fluid connection should be able to be produced in a simple and reliable manner. The known connectors can be used for this purpose, for example the known Hansen couplings. To establish a fluid connection for feeding fresh dialysate to the ultrafiltration unit and removing used dialysate from the ultrafiltration unit, a docking station is preferably provided so that the ultrafiltration unit can be connected to the supply device in a simple and reliable manner.

The filter of the ultrafiltration unit is preferably a replaceable filter which is designed for a single use (a disposable). The known filters comprise a first chamber and a second chamber, which are separated by a semipermeable membrane. The first chamber and second chamber of the known filters each have an inlet and an outlet. To connect the filter, the ultrafiltration unit comprises a first filter connection for the inlet of the first chamber of the filter and a second filter connection for the outlet of the first chamber of the filter, and comprises a third filter connection for the inlet of the second chamber of the filter and a fourth filter connection for the outlet of the second chamber of the filter.

A preferred embodiment of the ultrafiltration unit provides a first dialysate connection line, which connects the first dialysate connection to the third filter connection, and a second dialysate connection line, which connects the second dialysate connection to the fourth filter connection. As a result, a direct fluid connection is established between the relevant components. The connection lines can be tube lines which are either permanently installed or replaceable. Suitable connectors can be provided for replacing the lines.

A further preferred embodiment provides a fluid connection of the ultrafiltrate line portion, which leads to the inlet of the ultrafiltration pump, to the third filter connection and/or a fluid connection of the ultrafiltrate line portion, which leads to the inlet of the ultrafiltration pump, to the fourth filter connection, an ultrafiltrate line portion which leads to a container for holding ultrafiltrate being connected to the outlet of the ultrafiltration pump. The ultrafiltrate can thus be removed via one filter connection or the two filter connections. In the process, the relevant line portions can be connected to the filter connections either directly or via additional line portions. To break the fluid connection, shut-off valves or the like can also be provided in the line portions.

The extracorporeal blood circuit of the ultrafiltration unit comprises a first, arterial blood line leading away from the patient and a second, venous blood line leading to the patient.

The arterial blood line leads to the first filter connection of the filter so that blood can flow into the first chamber of the filter, while the venous blood line leads away from the second filter connection so that blood can flow out of the first chamber.

The blood lines are preferably component parts of a single-use (disposable) tube set. Preferably, the ultrafiltration pump is a roller pump into which the preferably venous blood line of the tube set can be inserted in a simple manner. For this purpose, the blood lines can have suitable connectors.

The ultrafiltration unit preferably comprises a control unit for the blood pump and the ultrafiltration pump, which unit can preferably have various configurations to ensure proper operation of the pumps. The control unit can, for example, specify the necessary speeds for the pumps, the control unit also being able to monitor the speed of the pumps. In addition, the control unit can also assume an alarm function.

In a particularly preferred embodiment, the control unit comprises electrical connections for establishing an electrical connection between the control unit of the ultrafiltration unit and a control unit of the device for supplying dialysate to the ultrafiltration unit such that the two control units can communicate with one another. The control units can have suitable interfaces for the data exchange. The electrical connections can have various designs. To establish the electrical connection, a docking station is preferably provided so that the ultrafiltration unit can be electrically connected to the supply device in a simple and reliable manner. The docking station preferably comprises all the connections required for the fluid connection and the electrical connection.

The ultrafiltration unit further comprises a user interface which can have various designs. The user interface can comprise an input unit and a display unit. The input unit can comprise one or more operating elements, for example switches or buttons, and the display unit can comprise a screen. The operation can, however, also take place by means of a touchscreen. In the simplest case, the input unit comprises just one operating element for switching the pumps on and off.

In another particularly preferred embodiment, the ultrafiltration unit is formed as a unit to be worn on the patient's body by means of straps so that the patient can carry the ultrafiltration unit with them without their movement being significantly restricted. The ultrafiltration unit can, for example, be in the form of a bag or a rucksack. It may, however, also be possible for the ultrafiltration unit to be in the form of a unit which is suspended on a movable stand. For this purpose, the ultrafiltration unit can have suitable fastening elements, for example hooks or eyelets.

The ultrafiltration unit preferably comprises a carrier unit which houses the blood pump and the ultrafiltration pump and which can also house the additional components of the ultrafiltration unit, for example the control unit. The ultrafiltrate can be collected in a container, for example in a pouch, which the patient can carry with them. The pouch is carried by the patient, preferably independently of the carrier unit. For this purpose, the container can also be in the form of a unit to be worn on the patient's body by means of straps.

Figure 2B:
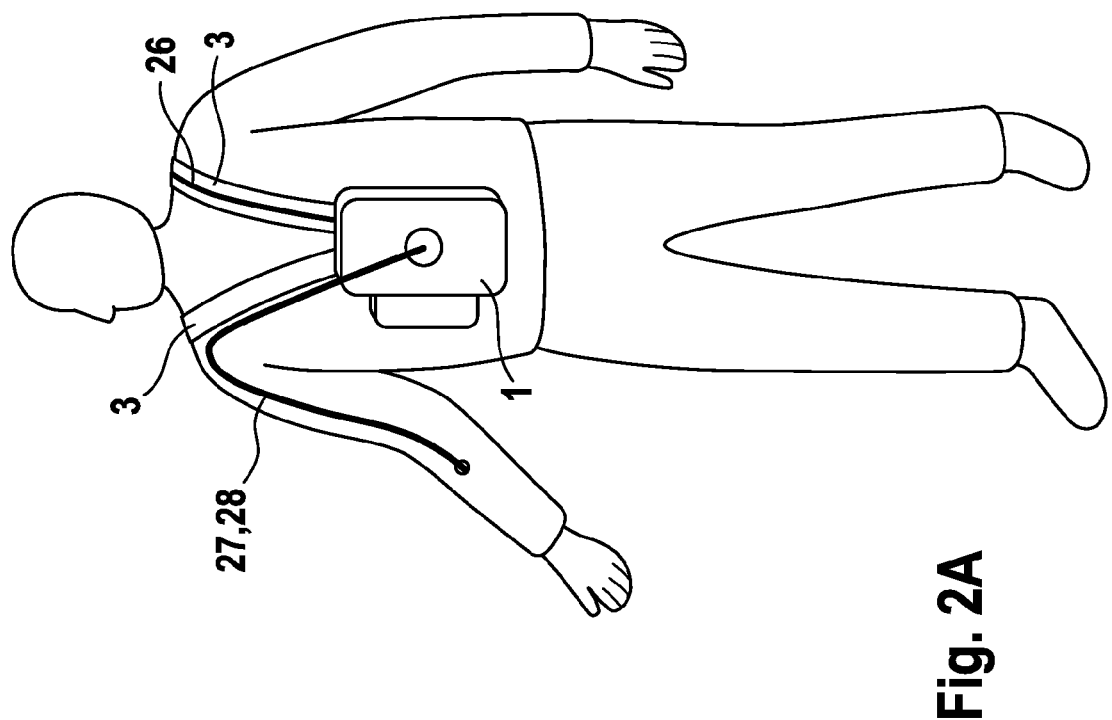
Figure 3:
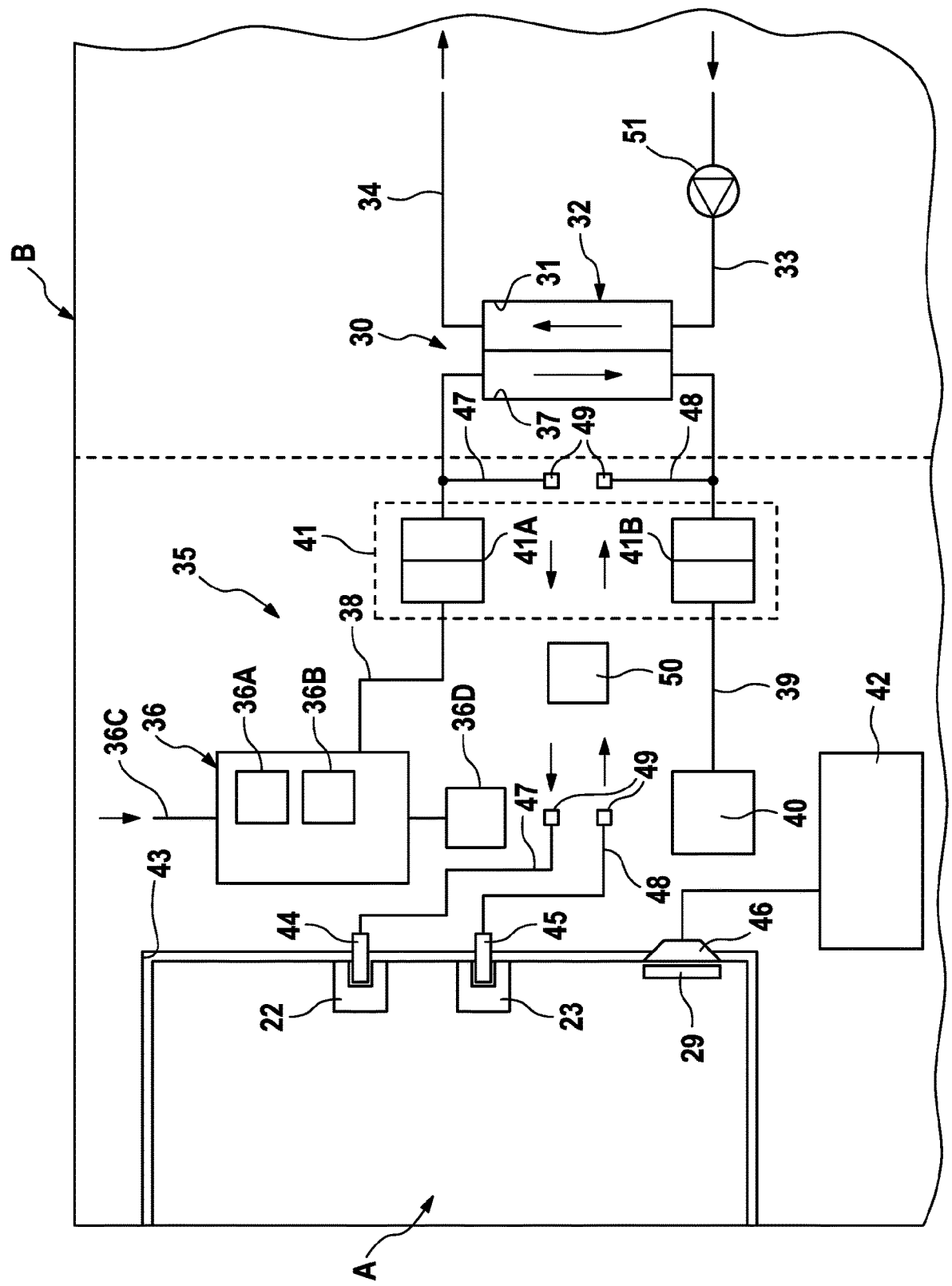

An embodiment of the invention will be explained in more detail below with reference to the drawings, in which:

FIG. 1A is a simplified schematic view of the ultrafiltration unit according to the invention, FIG. 1B is a side view of the ultrafiltration unit of FIG. 1A, FIG. 1C is a plan view of the ultrafiltration unit of FIG. 1A, FIG. 2A shows the carrier unit of the ultrafiltration unit, in the form of a side bag, FIG. 2B shows the container for holding the ultrafiltrate of the ultrafiltration unit, in the form of a rucksack, and FIG. 3 is a greatly simplified schematic view of the ultrafiltration unit according to the invention and the device according to the invention for supplying dialysate to the ultrafiltration unit.

FIGS. 1A, 1B and 1C are simplified schematic views of the essential components of the ultrafiltration unit according to the invention. The ultrafiltration unit comprises a carrier unit 1 containing the machine components and a container 2 for holding ultrafiltrate.

The carrier unit 1 is in the form of a shoulder bag or side bag, which comprises carry straps 3 on the sides so that the patient can hang the carrier unit 1 around their shoulders. FIG. 2A shows the patient together with the carrier unit 1. The container 2 for holding the ultrafiltrate is in the form of a rucksack which is worn on the patient's back by straps 4. FIG. 2B shows the patient together with the container 2. The container 2 can be a flexible plastics pouch.

The carrier unit 1 comprises a housing body 5 which houses an ultrafiltration pump 6 and a blood pump 7, in particular a roller pump. In the housing body 5 there is also a control unit 8, by means of which the ultrafiltration pump 6 and the blood pump 7 are controlled. On the upper face of the housing body 5, there is a user interface 9 which comprises an input unit 10 having switches or buttons 10A, 10B and a display unit 11 having a screen 11A.

On one of the two longitudinal sides, the housing body 5 comprises a mount 12 for inserting a filter 13 (dialyser), which is designed for single use. The filter 13 can be a conventional dialysis filter which is divided into a first chamber and a second chamber by a semipermeable membrane. The first chamber comprises a lateral inlet 14 and outlet 15 and the second chamber comprises a lateral inlet 16 and outlet 17. To connect the filter 13, the carrier unit 1 has a first filter connection 18 for the inlet 15 of the first chamber of the filter 13, a second filter connection 19 for the outlet 15 of the first chamber of the filter, a third filter connection 20 for the inlet 16 of the second chamber of the filter and a fourth filter connection 21 for the outlet 17 of the second chamber of the filter. These connections can be provided on one of the two longitudinal sides of the housing body. On the opposite longitudinal side of the housing body, there is a first dialysate connection 22 and a second dialysate connection 23 so that the ultrafiltration device A can be connected to a device B (not shown in FIG. 1A to 1C) for supplying dialysate to the ultrafiltration unit. A first dialysate connection line 24 connects the first dialysate connection 22 to the third filter connection 20 and a second dialysate connection line 25 connects the second dialysate connection 23 to the fourth filter connection 17. A line portion 26A of an ultrafiltration line 26 branches off from the first dialysate connection line 24 and a line portion 26B of the ultrafiltration line 26 branches off from the second dialysate connection line 25. The two line portions 26A, 26B of the ultrafiltration line 26 lead to the inlet of the ultrafiltration pump 6, and so ultrafiltrate can be removed from the second chamber of the filter 13 by means of the ultrafiltration pump 6. A further line portion 26C of the ultrafiltration line 26 connects the outlet of the ultrafiltration pump 6 to the inlet of the container 2 for holding the ultrafiltrate.

The extracorporeal blood circuit comprises an arterial blood line 27 having an arterial patient connection 27A, and a venous blood line 28 having a venous patient connection 28A, which are component parts of a tube set designed for single use. The arterial blood line 27 and venous blood line 28 can be directly connected to the first and second filter connections 18, 19, i.e. the filter connections are component parts of the disposable, or the blood lines can be provided with suitable connectors which allow for connection to filter connections permanently installed in the housing body. The arterial blood line 27 is inserted into the roller pump 7 so that the roller pump 7 conveys blood from the patient through the first chamber (blood chamber) of the filter 13 and the ultrafiltration pump 6 can remove ultrafiltrate from the second chamber of the filter.

For the purpose of data exchange, the control unit 8 comprises electrical connections 29 which are provided on one of the two longitudinal sides of the housing body 5.

The ultrafiltration unit A can contain additional components which, however, are not shown in FIG. 1A to 1C. For example, a valve can be provided in each case in the first and second connection line 24, 25 in order to be able to close off the lines for operating the ultrafiltration unit. However, it is also possible for the dialysate connections 22, 23 to be designed as connections which only open when suitable connectors are connected to the connections.

The ultrafiltration unit A can, however, also be operated in conjunction with the device B according to the invention for supplying dialysate to the ultrafiltration unit. FIG. 3 is a greatly simplified schematic view of the medical treatment system which comprises the ultrafiltration unit A and the supply device B. FIG. 3 only shows the modules of the supply device B that are essential for the invention.

The supply device B can be a blood treatment device which has a separate extracorporeal blood circuit to allow the supply device to be operated independently as a blood treatment device. It is also possible, however, for the supply device to only have the modules required for supplying the ultrafiltration unit.

In the present embodiment, the supply device B comprises an extracorporeal blood circuit 30, which, however, remains unused for the operation of the ultrafiltration unit A in conjunction with the supply device. The extracorporeal blood circuit 30 comprises an arterial blood line 33 leading to the blood chamber 31 of a dialyser 32 and a venous blood line 34 leading away from the blood chamber. To convey the blood in the extracorporeal blood circuit 30, a blood pump 51 is provided in the arterial blood line 33.

The dialysate system 35 of the supply device B comprises an apparatus 36, which can have various designs, for providing fresh dialysate. In the present embodiment, the apparatus 36 for providing fresh dialysate comprises a mixing unit 36A for mixing RO water and concentrate, and a heating unit 36B for heating the dialysate. The RO water can be fed via a water connection 36C and the concentrate can be provided in a concentrate container 36D. The apparatus 36 for providing fresh dialysate can also have additional known components, for example a degassing unit.

The dialysate system 35 of the supply device B, which can be operated independently as a blood treatment device, comprises a dialysate feed line 38 leading to the dialysate chamber 37 of the dialyser 32 and a dialysate removal line 39 which leads away from the dialysate chamber of the dialyser and leads to a drain or a container 40. In addition, the dialysate system 35 comprises a balancing unit 41 which is intended for balancing fresh and used dialysate and can have balancing chambers 41A, 41B.

To control all the machine components, a central control unit 42 is provided.

Only the apparatus 36 for providing fresh dialysate, the mixing unit 36A and heating unit 36B, the concentrate container 36C, the balancing unit 41 and the control unit 42 are required to supply dialysate to the ultrafiltration unit.

To connect the ultrafiltration unit A, which is in the form of a replaceable module, the supply device B comprises a docking station 43, which can be used to establish all the connections. The docking station 43 comprises a first connector 44 and a second connector 45 for the first and second dialysate connection 22, 23, respectively, of the ultrafiltration unit A, and an electrical connection piece 46 for the electrical connections 29 of the ultrafiltration unit. The first connector 44 is connected to a feed line 47 for fresh dialysate and the second connection 45 is connected to a removal line 48 for used dialysate. The feed line 47 and removal line 48 are connected at connection points 49 (only shown by way of indication in FIG. 3) on the dialysate system 35, to which points fresh dialysate can be removed from the dialysate system and used dialysate can be fed to the dialysate system, respectively. In the dialysate system, the fresh dialysate is provided by the apparatus 36 for providing fresh dialysate and is removed into the drain or container 40, the fresh and used dialysate being balanced by the balancing unit 41. For operation together with the ultrafiltration unit, a valve apparatus 50 (only shown by way of indication in FIG. 3) is provided which is designed such as to isolate the extracorporeal blood circuit 30.

If the ultrafiltration unit A is connected to the supply device B (FIG. 3), fresh dialysate flows through the second chamber (dialysate chamber) of the filter 13 of the ultrafiltration unit A whilst ultrafiltrate is removed from the second chamber via the ultrafiltration line 26. As a result, the ultrafiltration unit A can be used universally and not only allows for ultrafiltration between the dialysis treatments, but also for dialysis treatment in conjunction with the supply apparatus B.

The invention claimed is:

1. A portable ultrafiltration unit comprising a first pump that is a blood pump for conveying blood, a second pump that is an ultrafiltration pump for conveying ultrafiltrate, a first dialysate connection line, a second dialysate connection line, a first line portion that branches off the first dialysate connection line and is in fluid communication with the second pump, and a second line portion that branches off the second dialysate connection line and is in fluid communication with the second pump, wherein the first dialysate connection line is in fluid communication with the second pump via the first line portion, the second dialysate connection line is in fluid communication with the second pump via the second line portion, the portable ultrafiltration unit is in the form of a unit (A) to be connected to a stationary device (B) for supplying dialysate to the ultrafiltration unit such that a fluid connection can be established for feeding in fresh dialysate and removing used dialysate so that a dialysis treatment can be carried out using the ultrafiltration unit, and the ultrafiltration unit is in the form of a unit to be worn on the patient's body by means of straps.

2. The portable ultrafiltration unit according to claim 1, wherein the ultrafiltration unit (A) comprises a first dialysate connection in fluid communication with the first dialysate connection line for feeding fresh dialysate and a second dialysate connection in fluid communication with the second dialysate connection line for removing used dialysate.

3. The portable ultrafiltration unit according to claim 1, wherein the ultrafiltration unit (A) comprises a first filter connection for an inlet of a first chamber of a filter, which is divided into the first chamber and a second chamber by a semipermeable membrane, and a second filter connection for an outlet of the first chamber of the filter, and comprises a third filter connection for an inlet of the second chamber of the filter and a fourth filter connection for an outlet of the second chamber of the filter.

4. The portable ultrafiltration unit according to claim 3, wherein the first dialysate connection line connects the first dialysate connection to the third filter connection, and the second dialysate connection line connects the second dialysate connection to the fourth filter connection.

5. The portable ultrafiltration unit according to claim 4, wherein an ultrafiltrate line portion which leads to the inlet of the ultrafiltration pump is in fluid communication with the third filter connection and/or an ultrafiltrate line portion which leads to the inlet of the ultrafiltration pump is in fluid communication with the fourth filter connection, an ultrafiltrate line portion which leads to a container for holding ultrafiltrate being connected to the outlet of the ultrafiltration pump.

6. The portable ultrafiltration unit according to claim 4, wherein the ultrafiltration unit (A) comprises a first blood line leading to the first filter connection for feeding blood into the first chamber of the filter and a blood line leading away from the second filter connection for removing blood from the first chamber of the filter.

7. The portable ultrafiltration unit according to claim 3, wherein an ultrafiltrate line leads to a container for holding ultrafiltrate and is connected to an outlet of the ultrafiltration pump.

8. The portable ultrafiltration unit according to claim 3, wherein the ultrafiltration unit (A) comprises a first blood line leading to the first filter connection for feeding blood into the first chamber of the filter and a blood line leading away from the second filter connection for removing blood from the first chamber of the filter.

9. The portable ultrafiltration unit according to claim 2, wherein the ultrafiltration unit (A) comprises a first filter connection for an inlet of a first chamber of a filter, which is divided into the first chamber and a second chamber by a semipermeable membrane, and a second filter connection for an outlet of the first chamber of the filter, and comprises a third filter connection for an inlet of the second chamber of the filter and a fourth filter connection for an outlet of the second chamber of the filter.

10. The portable ultrafiltration unit according to claim 1, wherein the ultrafiltration unit (A) comprises a control unit for the blood pump and the ultrafiltration pump.

11. The portable ultrafiltration unit according to claim 1, wherein the control unit comprises electrical connections for producing an electrical connection between the control unit of the ultrafiltration unit (A) and a control unit of the device (B) for supplying dialysate to the ultrafiltration unit.

12. The portable ultrafiltration unit according to claim 1, wherein the ultrafiltration unit (A) comprises a user interface.

13. The portable ultrafiltration unit according to claim 1, wherein the ultrafiltration unit (A) comprises a carrier unit which houses the blood pump and the ultrafiltration pump.

14. A device for supplying dialysate to the portable ultrafiltration unit according to claim 1, comprising an apparatus for providing fresh dialysate, an apparatus for removing used dialysate, and a balancing unit for balancing fresh and used dialysate, wherein the device (B) for supplying the ultrafiltration unit (A) is designed such that a fluid connection can be established for feeding fresh dialysate to the ultrafiltration unit and removing used dialysate from the ultrafiltration unit so that a dialysis treatment can be carried out using the ultrafiltration unit.

15. The device according to claim 14 for supplying dialysate to the ultrafiltration unit (A), wherein the device (B) comprises a docking station for establishing a fluid connection for feeding fresh dialysate to the ultrafiltration unit (A) and removing used dialysate from the ultrafiltration unit.

16. The device according to claim 15 for supplying dialysate to the ultrafiltration unit (A), wherein the device (B) is in the form of a device for extracorporeal blood treatment which comprises an extracorporeal blood circuit and a dialysate system.

17. The device according to claim 14 for supplying dialysate to the ultrafiltration unit, wherein the device (B) is in the form of a device for extracorporeal blood treatment which comprises an extracorporeal blood circuit and a dialysate system.

18. A medical treatment system comprising the portable ultrafiltration unit (A) according to claim 1 and a device (B) for supplying the ultrafiltration unit (A), where the medical system is designed such that a fluid connection can be established for feeding fresh dialysate to the ultrafiltration unit (A) and removing used dialysate from the ultrafiltration unit (A) so that a dialysis treatment can be carried out using the ultrafiltration unit (A).

19. The portable ultrafiltration unit according to claim 1, further comprising a battery configured for battery-powered operation of the ultrafiltration unit.

* * * * *